United States Patent [19]

Isaza et al.

[11] Patent Number: 5,271,389
[45] Date of Patent: Dec. 21, 1993

[54] VENTILATOR CONTROL SYSTEM THAT GENERATES, MEASURES, COMPARES, AND CORRECTS FLOW RATES

[75] Inventors: Fernando J. Isaza, San Marcos; Stanley Y. Wong, Oceanside, both of Calif.

[73] Assignee: Puritan-Bennett Corporation, Carlsbad, Calif.

[21] Appl. No.: 836,773

[22] Filed: Feb. 12, 1992

[51] Int. Cl.$^5$ .................. A61M 16/00; A62B 7/00; A62B 9/02; F16K 31/02
[52] U.S. Cl. .................. 128/204.21; 128/204.22; 128/205.24
[58] Field of Search ............ 128/204.21, 204.26, 128/204.22, 204.23, 205.23, 716, 719, 724, 725, 205.24; 364/413.02, 413.03, 565, 569, 224.5, 224.6, 922.2–922.4, 922, 571.02, 571.05

[56] References Cited

U.S. PATENT DOCUMENTS

| | | | |
|---|---|---|---|
| 3,741,208 | 6/1973 | Jonsson et al. | 128/204.21 |
| 3,961,627 | 6/1976 | Ernst et al. | 128/204.21 |
| 3,972,327 | 8/1976 | Ernst et al. | 128/204.21 |
| 4,281,651 | 8/1981 | Cox | 128/204.23 |
| 4,345,612 | 8/1982 | Koni et al. | 128/204.21 |
| 4,421,113 | 12/1983 | Gedeon et al. | 128/204.23 |
| 4,971,049 | 11/1990 | Rotariu et al. | 128/204.21 |

*Primary Examiner*—Edgar S. Burr
*Assistant Examiner*—Kimberly L. Asher
*Attorney, Agent, or Firm*—Fulwider Patton Lee & Utecht

[57] ABSTRACT

The present invention provides a system and method for providing an improved correction to an input flow control signal to a flow control valve in a ventilator system. The correction as derived from a sum of the error in the flow rate actually delivered as compared with the desired flow rate for each control interval in a breath with the sum of past errors corresponding to control intervals in past breaths to generate a cumulative error signal for application in the control interval in a next breath. The cumulative error signal is stored as the sum of previous sustained errors arising periodically in the system for each control interval of previous breaths, and is integrated with the current error signal for each control interval to generate an integrated correction component signal. The input flow control signal is summed with the integrated correction component to generate a corrected command flow signal to the flow control valve.

9 Claims, 4 Drawing Sheets

FIG. 2 *PRIOR ART*

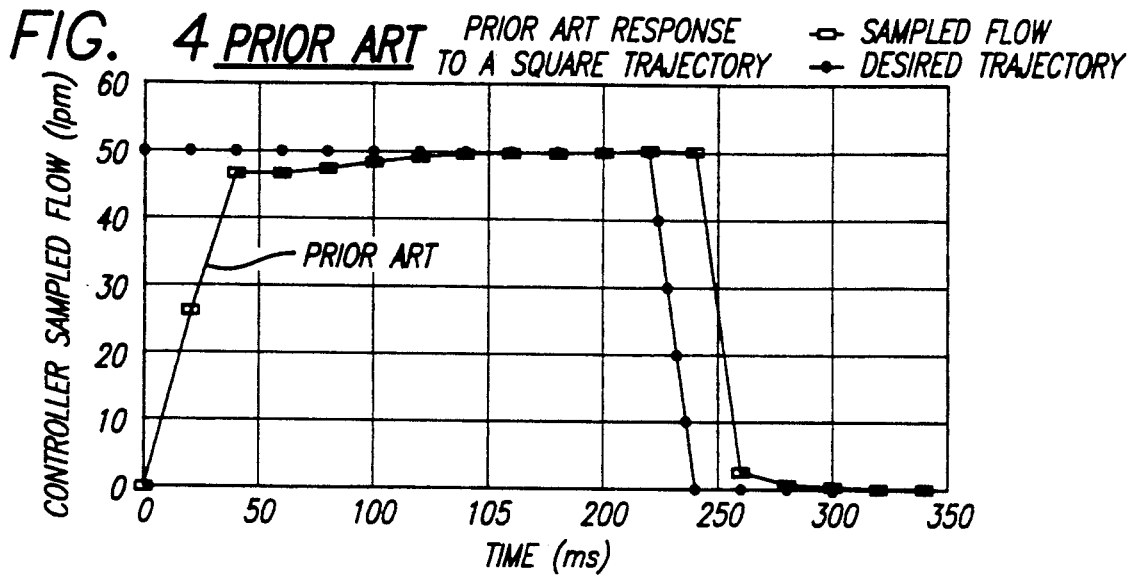
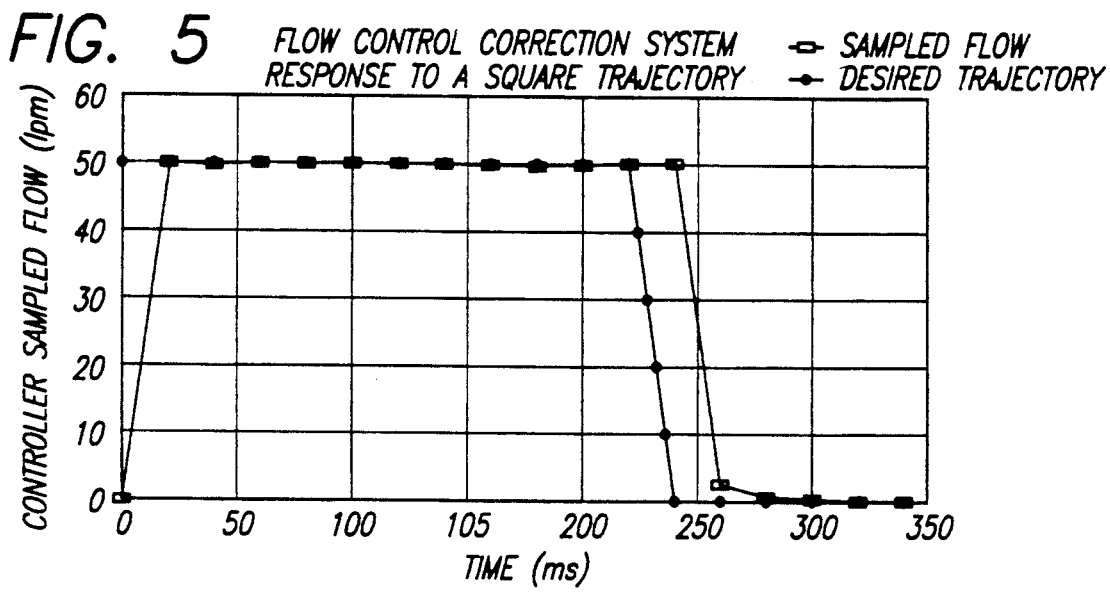
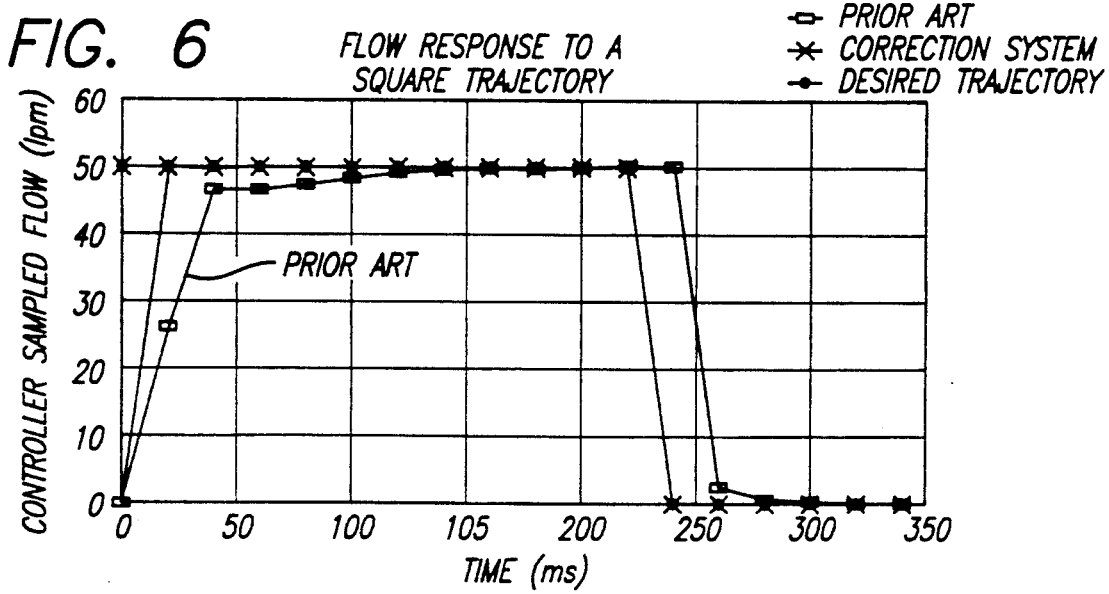

VENTILATOR CONTROL SYSTEM THAT GENERATES, MEASURES, COMPARES, AND CORRECTS FLOW RATES

BACKGROUND OF THE INVENTION

1. Field of the Invention

This invention relates generally to controllers for systems having periodic output functions with measurable parameters such as pressure, flow, motion, and the like, and more particularly relates to an electronically controlled ventilator system for providing respiratory gas to a patient, and an improved system and method for discrete time control of ventilation flow during patient breaths.

2. Description of Related Art

Breathing ventilator systems conventionally provide breathing gas to a patient for pressure supported breath assistance at a pressure support level as high as 70 centimeters of water, or minimal pressure, usually no more than 2 centimeters of water above baseline.

Conventional ventilators typically provide breath inhalation support at regular intervals, or at intervals triggered by a patient's spontaneous inspiration effort. Errors in the delivery of gas flow as compared to the desired gas flow at the appropriate time can occur due to lag time between the onset of patient inspiratory effort and actual valve response time, regulator response, and valve gain variations. Although typical flow controllers may utilize a feedforward flow control gain component and various types of feedback error correction, such as proportional, integral, or derivative error feedback control, to compensate for real time disturbances that occur in the system, such systems frequently have difficulty in correcting for any sustained errors that occur periodically in the system.

Until recently, such inaccuracy in flow control of ventilators has hampered application of ventilators for infant and neonatal patients. It would therefore be desirable to provide a system for adaptive response to periodic disturbances in a ventilator flow system, based upon past system performance with the correction including an integration of flow rate errors during all of the previous breath control intervals for a patient. It would be desirable for every control interval of patient assisted breathing to be affected by a correction component, so that the output flow rate matches the actual demands on the system.

A major factor in assisting patient breathing is the energy required by a patient to trigger and obtain an adequate flow of respiratory gas. It would therefore be desirable to improve the accuracy of flow control to reduce this energy requirement in the work of breathing.

SUMMARY OF THE INVENTION

The present invention provides a system and method for providing a correction to a signal controlling a flow control valve in a ventilator system. The correction component integrates the difference between the desired flow rate and the actual delivered flow rate for each control interval for each breath with the sum of past errors corresponding to the same control interval of the past breaths to generate a corrected command flow signal to be applied on the corresponding appropriate interval to the flow control valve.

Briefly and in general terms, the system of the present invention for controlling the rate of flow of a respiratory gas supplied by a ventilation system for supporting breaths of a patient intubated on the ventilation system comprises means for generating an input flow control signal based upon a desired rate of flow for each control interval in the current breath, means for measuring the actual rate of flow in the flow path of the ventilation system for each control interval in the current breath, means for generating a current error signal representing the difference between the actual rate of flow and the desired rate of flow for each control interval in the current breath, and means for summing each error signal for each control interval in the current breath with the sum of the previous error signals for each control interval of the previous breaths to generate a correction component signal to be used at the appropriate control intervals in the next breath. The system includes means for storing the correction component signal as the sum of previous error signals of each control interval of the previous breaths, and means for summing the error signal and the correction component control signal for each control interval to generate a signal to be applied to a conventional integrator element.

Means are also preferably provided for generating a predetermined valve gain feedforward component for each control interval of each breath and for summing the output signal resulting from the conventional integrator with the feedforward correction component, for each control interval, to generate a command flow signal for the flow control valve.

In the currently preferred method of the invention, controlling the rate of flow of the respiratory gas supplied by the ventilation system involves generating input flow control signals based upon the desired flows for all control intervals for each breath, measuring the actual rate of flow in the flow path for all control intervals, comparing the rate of flow in the flow path with the desired rate of flow to generate the current error signal for all control intervals representing the difference between the actual rate of flow and the desired rate of flow for each breath and summing each current error signal for each control interval with the sum of the previous error signals for each control interval for each past breath, to generate the correction component signals for use in the next breath. The correction component signal, for a given control interval in a breath, is preferably stored as the sum of the previous error signals for the corresponding control interval of the past breaths slimmed with the current error signal for the given control interval for the current breath to generate a correction component signal for the next breath.

A predetermined valve gain is preferably used in the feedforward component to generate the feedforward element of the command flow signal. The signal resulting from the summation of the error signal and the correction component signal is preferably processed by a conventional integrator, to generate a second element in the command flow signal. This element of the command flow signal is preferably added to the feedforward component to generate the command flow signal for operating the flow control valve. Controlling the flow control valve in this manner thus allows the ventilation system to deliver the desired rate of flow for each breath.

Other aspects and advantages of the invention will become apparent from the following detailed description and the accompanying drawings which illustrate by way of example the features of the invention.

BRIEF DESCRIPTION OF THE DRAWINGS

FIG. 4 is a graph showing a flow response of a prior art controller;

FIG. 5 is a graph of a flow response of a controller according to the present invention as illustrated in FIG. 3; and FIG. 6 is a chart comparing the accuracy of flow delivery for a prior art controller and for a controller according to the invention.

DETAILED DESCRIPTION OF THE PREFERRED EMBODIMENT

Figure 1:
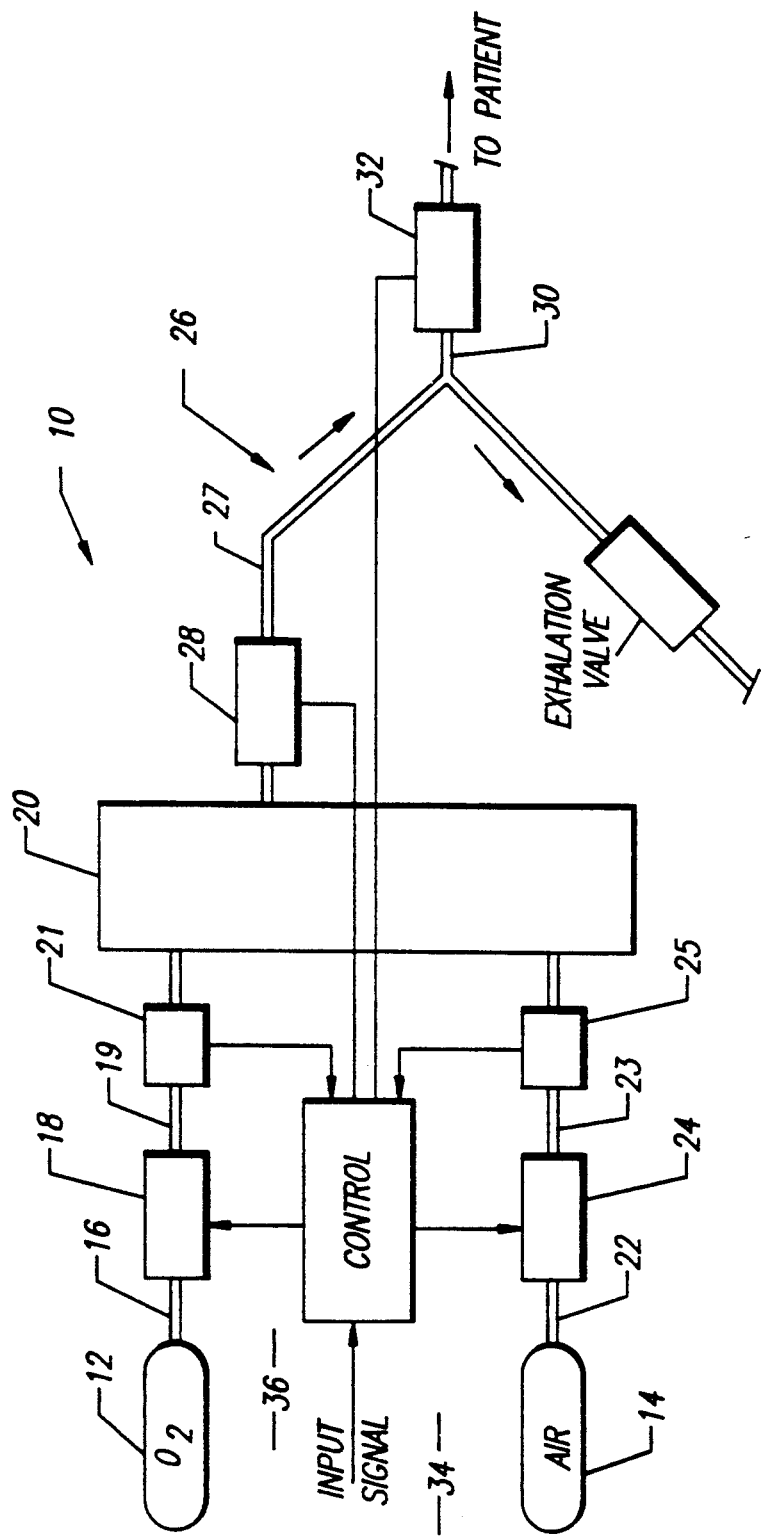
FIG. 1 is a diagram of a conventional ventilation system.

As is shown in the drawings for purposes of illustration, the invention is embodied in a system for providing a corrected flow control of respiratory gas supplied by a ventilation system, to improve accuracy of the rate of flow delivered by the system, and to reduce the patient work of breathing. The flow control correction system may be used in an open or closed patient ventilation system, having a source of respiratory gas, a flow path for communicating a respiratory gas to a patient intubated in the ventilation system, a flow control valve for controlling the rate of flow in the flow path, control means for generating a control signal for operating the flow control valve at least once in a predetermined control interval in a breath to deliver a desired rate of flow in the flow path for each breath supported by the ventilation system, and a flow sensor in the flow path connected to the control means for measuring the actual rate of flow in the flow path. An input signal based upon the rate of flow of respiratory gas required to support a patient breath is modified by the flow control correction system of the invention to provide a command flow signal to the flow control valve.

The respiratory gas is preferably enriched with a higher concentration of oxygen than normal, so that the source of respiratory gas may include more than one individual gas source, and may also include a device for mixing various proportions of the individual gases.

Figure 2:
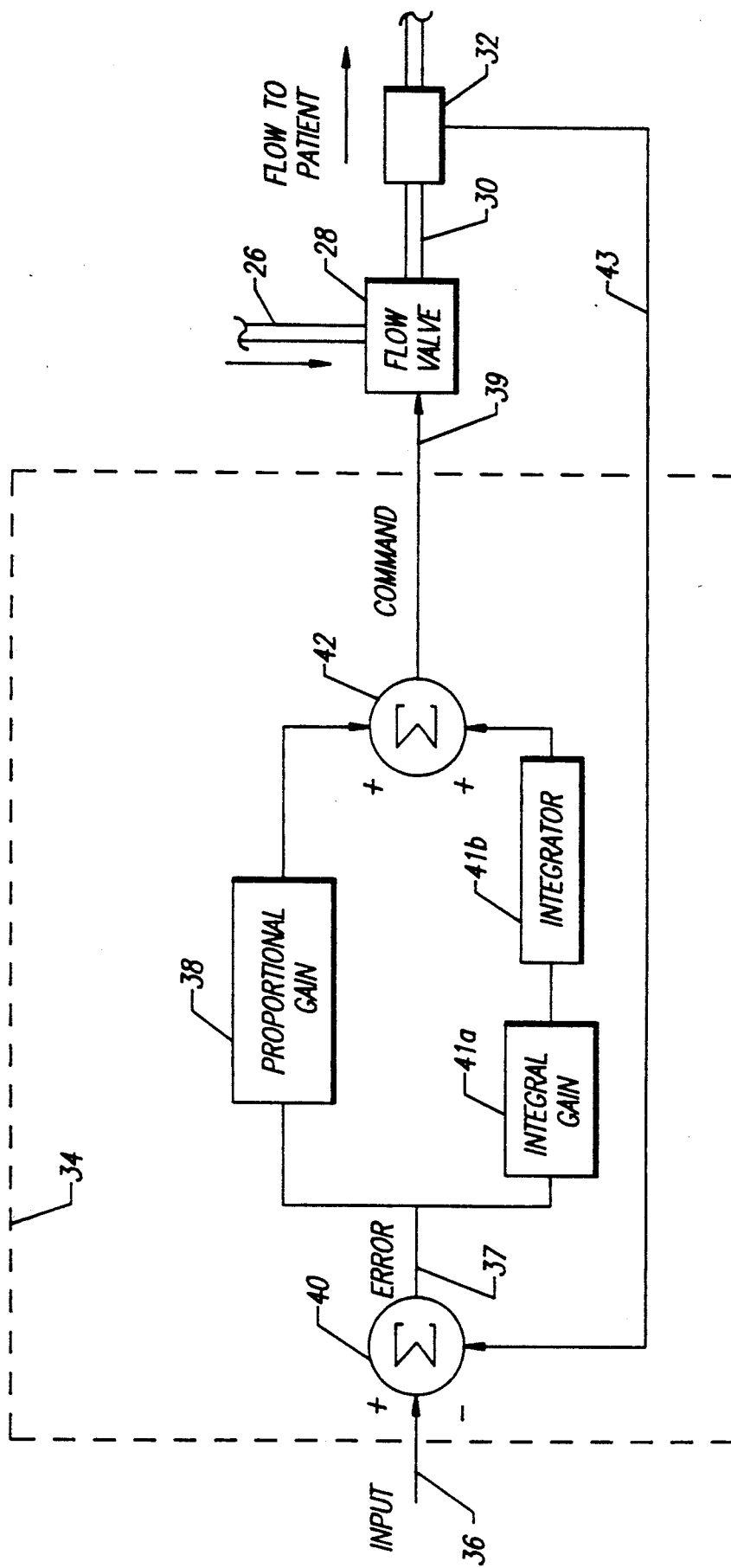
FIG. 2 is a block diagram of a prior art flow controller.

Accordingly, with reference to FIGS. 1 and 2, an exemplary prior art ventilation system 10 to which the flow control correction system of the invention may be applied typically includes a source of oxygen gas 12, which is typically a pressurized tank of oxygen, and a source of air 14, which may also consist of a high pressure tank or air compressor, which can supply air as needed from the ambient atmosphere. Other conventional sources of pressurized oxygen and air in hospital settings would also be appropriate. The source of oxygen is connected by a duct 16 to a proportional solenoid valve 18 which is in turn connected by duct 19 to a mixing chamber 20. A flow sensor 21 is preferably mounted in or connected to the duct 19 for measuring the rate of flow of oxygen actually delivered to the mixing chamber. The source of air is similarly connected by an air supply duct 22 to a proportional solenoid 24 for supplying air as needed to the mixing chamber via the duct 23, which also preferably includes a flow sensor 25 for measuring the actual rate of air flow delivered to the mixing chamber. Valves other than proportional solenoid valves that function in a similar manner may also be appropriate. The mixed gases can then be delivered to the patient through the patient airway generally indicated as 26. The patient airway can include, in a prefered embodiment, conduit 27, patient wye 30 and associated conduits for inhalation and exhalation. The patient airway 26 can also include a patient airway flow control valve 28 which controls the rate of flow of respiratory gas through the patient wye 30. A flow rate and/or pressure sensor 32 is typically placed within the patient airway for measuring the rate of flow or pressure level from the flow control valve through the patient airway. In a presently preferred embodiment, the sensor 32 can be placed downstream of the wye 30.

Referring to FIG. 2, the flow rate sensor is connected to a controller 34 for controlling the flow control valve based upon an input signal 36 representing the desired flow rate, which can be based upon patient respiratory demand based upon the flow rate and/or pressure measured in the patient wye, or which can be a stored value representing a predetermined flow level. The patient wye typically also includes a flow path for exhalation (not shown) which can also be monitored as desired.

The prior art electronic controller 34 shown in greater detail in FIG. 2 preferably includes a microprocessor for controlling all of the functions of the ventilator control system, and is also preferably connected to the oxygen and air supply flow valves 18 and 24, the flow rate sensors 21 and 25, and any additional flow meters, such as an exhalation flow meter. The electronic controller 34 typically also compares the rate of flow in the patient wye with a predetermined flow threshold level to detect changes in the flow due to inhalation efforts by the patient, and exhalation efforts by the patient, for purposes of triggering initiation of the control for the desired operation of the patient airway flow control valve 28, and to determine necessary corrections of the input signal for a desired flow rate to generate a command signal to the patient airway flow control valve to produce an actual flow rate at the desired rate in the patient airflow path. The electronic controller also preferably controls the proportional mixing through the oxygen and air supply valves, and adjusts the patient airway flow control valve to the appropriate state when exhalation efforts of the patient are detected.

The energy expended by a patient while breathing on a mechanical ventilator is related to not only the energy required to trigger gas delivery by the ventilator, but is also directly related to the accuracy of the volume of gas delivered to the patient. The flow control correction system of the invention is designed to improve the accuracy of control of the flow rate of gas delivered to the patient to reduce the energy required to be expended by the patient in breathing. This is accomplished by the division of the period of time from one breath to the next into a number of control intervals, and the implementation of a correction component for every control interval in the breath in a way such that for each breath of the patient the accuracy of delivery and the system response are improved. The correction component allows the control system to provide an adaptive response to compensate for sustained errors inherent to the system being controlled as well as to periodic disturbances, in a manner which a conventional controller is not able to do.

As is illustrated in FIG. 2, the prior art flow controller 34 typically includes a proportional gain amplifier means 38 such as an adjustable amplifier circuit or the like, which is connected to receive the error signal 37 for adding a proportional gain component to the error signal 37 to generate the basic command flow rate signal 39 to the flow control valve 28. The flow rate sensor 32 generates a flow rate measurement signal 43 which is compared at the comparator summing element 40 with the desired flow signal to generate an error signal 37, which is typically amplified by an integral gain element 41a and integrated by a conventional integrator element 41b with previous error signals, and which is then summed by summing element 42 with the basic amplified command signal to provide an integrated proportional command signal 39 to the flow control valve 28.

Figure 3:
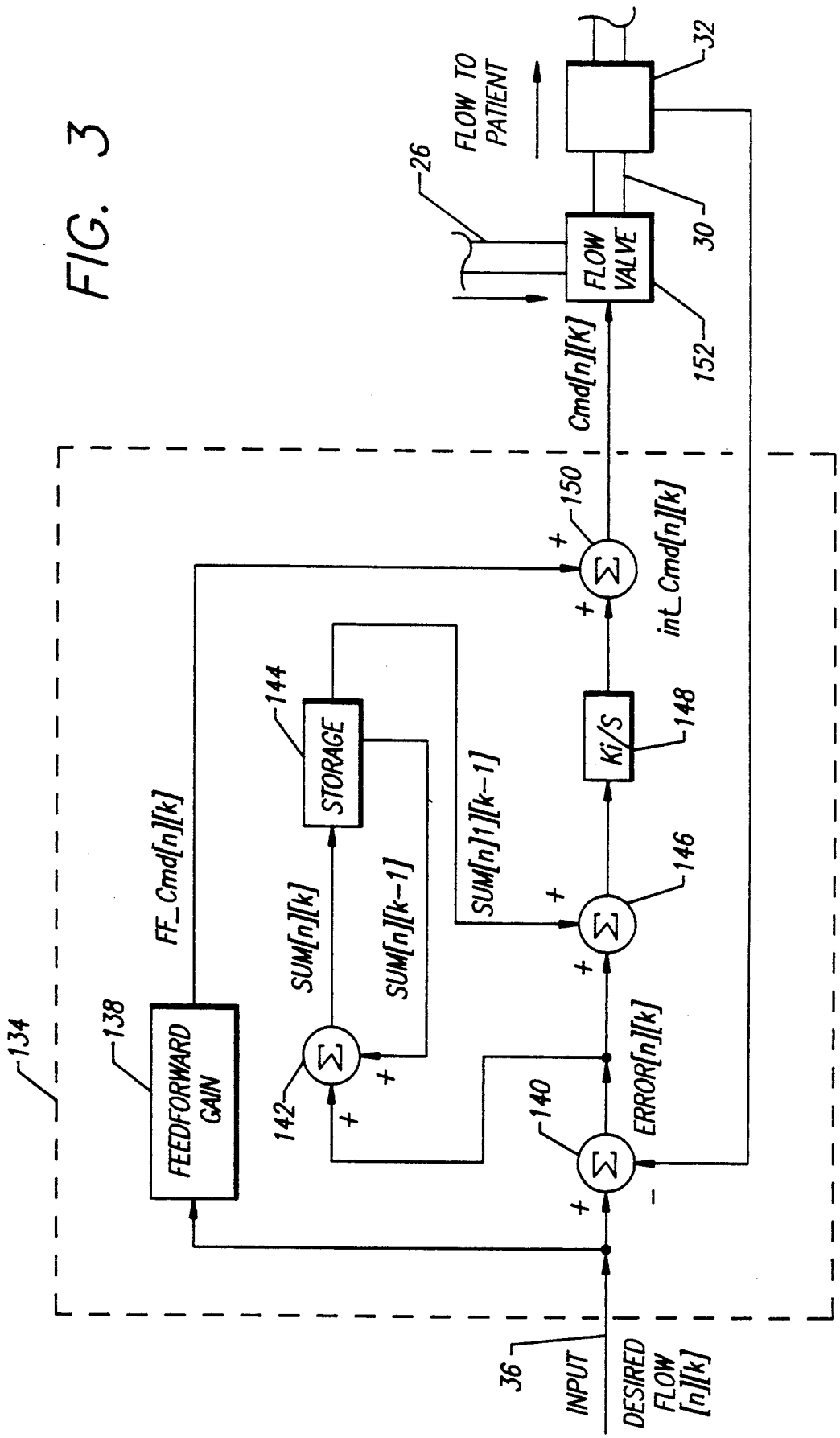
FIG. 3 is a block diagram of the flow control correction system of the invention.

As is illustrated in FIG. 3, the flow control correction system of the present invention preferably includes a means for integrating past flow rate delivery errors as a correction component for each control interval within each breath. This correction component is preferably added to the current error in delivery of flow rate for a patient breath to provide a signal input to a conventional integrator element which integrates the signals generated in previous control intervals within that breath. The correction component is further preferably added to feedforward flow control valve gain component to provide a corrected command signal for achieving the desired flow rate.

Thus, a controller 134 implementing the preferred embodiment of the invention is adapted to be used with a conventional ventilation system 10, in place of the prior art controller 34. A desired flow rate input signal 36 for a desired flow in a breath control interval number [n] for a particular breath number (k] is preferably received by valve feedforward gain means 138, such as an amplifier circuit, or the like for generation of a feedforward valve flow rate gain component to the desired flow rate input signal to overcome initial resistances and limitations of the system in delivering patient flow requirements before adequate feedback has been established. Alternatively, the feedforward gain element 138 may be omitted, although the control system would be less efficient in this configuration.

The flow rate measurement signal for each control interval in a breath generated by the flow meter 32, is received by the summing comparator element 140 which compares the input signal 36 with the actual flow rate measurement signal, to generate the current flow rate error signal [n][k] for the current control interval number [n] in the current individual breath number [k]. The current flow rate error signal is received by the summing element 142 which sums the instantaneous current error signals for each control interval in a breath with the sum of all previous corresponding error signals that occurred prior to the current breath number [k]. This sum of the current error signal (error [n][k]) for the current control interval and all previous error signals (sum [n][k−1]) for the current interval is stored in a storage or memory means 144 for use as a cumulative error signal for the corresponding control interval [n] of the next breath [k+1]. The cumulative error signal (sum [n][k−1]) represents sustained errors arising periodically in the system. The summing element 146 receives and sums the current error signal [n][k] for the control interval in a breath from summing element 140 with the cumulative error signals [n+1][k−1] from the storage means 144 to provide a signal which is preferably applied to a conventional integrator 148, with gain $k_I$, for generation of an integrated signal (Int Cmd [n][k]). The integrated signal is then added at summing element 150 with the feedforward command signal component (FFCmd [n][k]) to form the flow command signal (Cmd [n][k]) for application to the flow control valve 152, which is preferably a proportional solenoid valve.

As can be seen from FIGS. 4, 5 and 6, for a typical set of desired values for patient airway flow rate providing a sharp onset of flow, a constant flow rate for the period of inspiration assistance, and a relatively sharp cessation of flow known generally as a SQUARE trajectory, the flow control correction system of the invention approaches the desired trajectory more rapidly than the prior art controller does. Thus, assuming that the programmed trajectory of flow control is correct for the patient, the energy required of the patient for breathing should thereby be reduced.

It should be understood that while the valve feedforward gain element and the conventional integrator make for a more efficient control system, they can optionally be omitted from the controller, and the correction component can in itself correct for sustained errors that occur periodically in the ventilation system.

Thus, in the foregoing description, it has been demonstrated that the system and method of the invention allow for increased accuracy of flow rate delivery for reduction of patient work of breathing, by determining an error correction component which allows for adaptive response to real time disturbances which occur periodically in the ventilator system. It should be understood that the invention is also broadly applicable to controllers for systems having periodic output functions with measurable parameters such as pressure, flow, motion, and the like, so that the invention is not limited to use in controllers for ventilator systems.

While a particular form of the invention has been illustrated and described, it will be apparent that various modifications can be made without departing from the spirit and scope of the invention. Accordingly, it is not intended that the invention be limited, except as by the appended claims.

We claim:

1. A ventilator control system for controlling the rate of flow of a respiratory gas supplied by a ventilation system for supporting breaths of a patient intubated on the ventilation system, said ventilator control system comprising;

means for generating an input flow control signal based upon a desired rate of flow for a control interval in a current breath;

means for measuring an actual rate of flow in the ventilation system and generating a flow rate signal representing the actual rate of flow;

means for comparing said actual rate of flow with said desired rate of flow, and generating a current error signal representing the difference between the actual rate of flow and the desired rate of flow for each said control interval in each current breath;

means for summing each current error signal for each said control interval in each current breath with a sum of previous error signals for each said control interval of previous breaths to generate a correction component signal for application in said control interval in a next breath;

means for storing said correction component signal as the sum of previous error signals of each said control interval of previous breaths;

means for integrating said current error signal and said correction component signal for each said control interval to generate an integrated correction component signal; and means for summing said input flow control signal and said integrated correction component to generate a command flow signal for said ventilation system.

2. The system of claim 1, further including means for modifying said input flow control signal to include a predetermined valve gain feedforward component for each said control interval of each breath, and means for summing said feedforward component with said input flow control signal to generate a corrected input flow control signal for each said control interval in each current breath.

3. A method of controlling the rate of flow of a respiratory gas supplied by a ventilation system for supporting breaths of a patient intubated on the ventilation system, the method comprising the steps of:

generating an input flow control signal based upon said desired rate of flow for each control interval in a current breath;

measuring the actual rate of flow in the flow path and generating a flow rate signal representing the actual rate of flow in the ventilation system;

comparing the actual rate of flow with the desired rate of flow, and generating a current error signal representing the difference between the actual rate of flow and the desired rate of flow for each said control interval in each current breath; and summing each said current error signal for each said control interval in each current breath with a sum of previous error signals for each said control interval of previous breaths to generate a correction component signal for application in said control interval in a next breath;

storing said correction component signal as the sum of previous error signals of each said control interval of previous breaths;

integrating said current error signal and said correction component for each said control interval to generate an integrated correction component signal; and summing said flow control signal and said integrated correction component signal to generate a command flow signal for said ventilation system.

4. The method of claim 3, further comprising the step of modifying said input flow control signal by adding a predetermined valve gain feedforward component to said input flow control signal to generate a corrected flow control signal, for each said control interval in each current breath.

5. A method of controlling the rate of flow of a respiratory gas supplied by a ventilation system for supporting breaths of a patient intubated on the ventilation system, the method comprising the steps of:

generating an input flow control signal based upon said desired rate of flow for each control interval in a current breath;

measuring the actual rate of flow in the flow path and generating a flow rate signal representing the actual rate of flow in the ventilation system;

comparing the actual rate of flow with the desired rate of flow, and generating a current error signal representing the difference between the actual rate of flow and the desired rate of flow for each said control interval in each current breath; and summing each said current error signal for each said control interval in each current breath with a sum of previous error signals for each said control interval of previous breaths to generate a correction component signal for application in said control interval in a next breath.

6. A ventilator control system for controlling the rate of flow a respiratory gas supplied by a ventilation system for supporting breaths of a patient intubated on the ventilation system, comprising a source of respiratory gas, a flow path between said source of respiratory gas and in fluid communication with a patient, a flow control valve for controlling the rate of flow in said flow path, control means for generating a control signal for operating said flow control valve at least once in a predetermined control interval in a breath to deliver a desired rate of flow in said flow path for each said control interval in that breath, and a flow sensor in said flow path connected to said control means for measuring the actual rate of flow in said flow path, said ventilator control system further comprising;

means for generating an input flow control signal based upon said desired rate of flow for each control interval in a current breath;

means for measuring the actual rate of flow in the flow path and generating a flow rate signal representing the actual rate of flow in the flow path;

means for comparing said rate of flow in said flow path with said desired rate of flow, and generating a current error signal representing the difference between the actual rate of flow and the desired rate of flow for each said control interval in that breath;

means for summing each said current error signal for each said control interval in said breath with a sum of previous error signals for each said control interval of the previous breaths to generate a correction component signal for application in said control interval in a next breath;

means for storing said correction component signal as the sum of previous error signals of each said control interval of those previous breaths;

means for integrating said current error signal and said correction component signal for each said control interval to generate an integrated correction component signal; and means for summing said input flow control signal and said integrated correction component signal to generate a command flow signal for said flow control valve.

7. The system of claim 6, further including means for modifying said input flow control signal to include a predetermined valve gain feedforward component for each said control interval of each breath, and means for summing said feedforward component with said input flow control signal to generate a corrected input flow control signal for each said control interval in that breath, said means for modifying overcoming initial flow resistances inherent in the ventilator system.

8. A method of controlling the rate of flow of respiratory gas supplied by a ventilation system for supporting breaths of a patient intubated on the ventilation system, comprising providing a ventilation system including a source of respiratory gas, a flow path for said respiratory gas in fluid communication with a patient, a flow control valve for controlling the rate of flow in said flow path, control means for generating a control signal for operating said flow control valve at least once in a predetermined control interval in a breath to deliver a desired rate of flow in said flow path for each said control interval in that breath, and means for measuring the rate of flow in said flow path connected to said control means for generating a flow rate signal representing the actual rate of flow in said flow path, and further comprising the steps of:

generating an input flow control signal based upon said desired rate of flow for each control interval in a current breath;

measuring the actual rate of flow in the flow path and generating a flow rate signal representing the actual rate of flow in the flow path;

comparing the rate of flow in said flow path with the desired rate of flow in said flow path, and generating a current error signal representing the difference between the actual rate of flow and the desired rate of flow for each said control interval in said breath;

summing each said current error signal for each said control interval in said breath with a sum of previous error signals for each said control interval of previous breaths to generate a correction component signal for application in said control interval in a next breath;

storing said correction component signal as the sum of previous error signals of each said control interval of the previous breaths;

integrating said current error signal and said correction component for each said control interval to generate an integrated correction component signal; and summing said flow control signal and said integrated correction component signal to generate a command flow signal for said control valve.

9. The method of claim 8, further comprising the steps of modifying said input flow control signal by adding a predetermined valve gain feedforward component to said input flow control signal to generate a corrected flow control signal, for each said control interval in that breath and thereby correcting for initial flow resistances within said system.

* * * * *

UNITED STATES PATENT AND TRADEMARK OFFICE
CERTIFICATE OF CORRECTION

PATENT NO. : 5,271,389
DATED : December 21, 1993
INVENTOR(S) : Fernando J. Isaza; Stanley Y. Wong It is certified that error appears in the above-indentified patent and that said Letters Patent is hereby corrected as shown below:

At Column 2, line 49, delete "slimmed" and insert "summed".

At Column 5, line 33, delete "(k]" and insert "[k]".

Signed and Sealed this

Twenty-fifth Day of October, 1994

Attest:

BRUCE LEHMAN

*Attesting Officer*          *Commissioner of Patents and Trademarks*